(12) United States Patent
Siegel (10) Patent No.: US 9,615,706 B1
(45) Date of Patent: Apr. 11, 2017

(54) FLOOR ASPIRATOR

(71) Applicant: David Siegel, Warren, NJ (US)

(72) Inventor: David Siegel, Warren, NJ (US)

(*) Notice: Subject to any disclaimer, the term of this patent is extended or adjusted under 35 U.S.C. 154(b) by 0 days.

(21) Appl. No.: 15/098,364

(22) Filed: Apr. 14, 2016

(51) Int. Cl.
| | |
|---|---|
| A47L 9/02 | (2006.01) |
| A47L 7/00 | (2006.01) |
| A47L 9/06 | (2006.01) |

(52) U.S. Cl.
CPC .......... *A47L 7/0009* (2013.01); *A47L 9/0686* (2013.01)

(58) Field of Classification Search
CPC . A47L 7/0009; A47L 9/0686; B05C 17/0212; B05C 17/0217; B05C 17/022; B05C 17/0232
See application file for complete search history.

(56) References Cited

U.S. PATENT DOCUMENTS

| | | | |
|---|---|---|---|
| 5,014,389 A | 5/1991 | Ogilvie et al. | |
| 5,032,184 A | 7/1991 | Ogilvie et al. | |
| 5,437,651 A * | 8/1995 | Todd | A61M 1/0088 |
| | | | 15/420 |
| 5,655,258 A | 8/1997 | Heintz | |
| 5,720,078 A | 2/1998 | Heintz | |
| 5,741,237 A | 4/1998 | Walker | |
| 5,827,246 A | 10/1998 | Bowen | |
| 5,906,025 A | 5/1999 | Johnson | |
| 6,136,098 A | 10/2000 | Tribastone | |
| 6,513,192 B1 * | 2/2003 | Pearlstein | A47L 9/02 |
| | | | 15/415.1 |
| 7,901,389 B2 | 3/2011 | Mombrinie | |
| 8,317,774 B2 | 11/2012 | Adahan | |
| 2005/0197639 A1 | 9/2005 | Mombrinie | |
| 2010/0060118 A1 * | 3/2010 | Tafil | A47L 23/24 |
| | | | 312/237 |
| 2012/0210539 A1 | 8/2012 | Diminick et al. | |
| 2015/0342425 A1 * | 12/2015 | Esposito | A47L 7/0004 |
| | | | 134/21 |

OTHER PUBLICATIONS

DeRoyal, Puddle Guppy™, http://www.deroyal.com/medicalproducts/surgicalandacutecare/product.aspx?id=ac-wastefluid-puddleguppy, accessed May 4, 2016.

* cited by examiner

Primary Examiner — Dung Van Nguyen
(74) Attorney, Agent, or Firm — Gearhart Law LLC (57) ABSTRACT

A floor aspirator is provided. This aspirator features a suction head, having a perimeter, a top surface, a bottom surface, at least one drain between the top surface and the bottom surface, where the at least one drain spans the top surface and the bottom surface, a suction port, which is made up of a suction hole, and a fluid conduit, and a filter, disposed on the suction hole. There exist embodiments where multiple suction ports are featured, as well as embodiments where the top surface is graded towards the at least one drain.

21 Claims, 5 Drawing Sheets

FLOOR ASPIRATOR

CLAIM OF PRIORITY

This application does not claim priority to any patent or patent application.

FIELD OF THE EMBODIMENTS

The present invention and its embodiments relate to an improved floor aspirator, in particular a disposable floor aspirator designed to quickly remove fluids from the floor of an operating room.

BACKGROUND OF THE EMBODIMENTS

During various procedures fluids are released, which often fall onto the floor. For example, during a surgical procedure, not only can blood and other body fluids spill onto the floor, some procedures irrigate a surgical site with copious amounts of saline solution, which is then allowed to spill onto the floor.

It is highly desirable to quickly get these fluids away from the surgeon's feet to reduce the risk of slipping. Also, fluids released during surgery can spread infections and this risk is greatly enhanced the longer the surgeon stands or walks in these fluids.

In many surgical procedures some sort of suction device is used in the operating room to address this issue. Frequently, this suction device is used to remove blood as well as other fluids, gases, tissues, and other foreign matter that accumulates on the floor of an operating room during an operation or other procedure. As this fluid accumulation is nearly ubiquitous with surgery, there is a significant need to quickly and easily remove fluids from an operating room floor. Also of consideration is the time to clean the operating rooms between surgeries. The present invention allows quick cleaning of an operating room floor improving turnover times between surgeries.

Because this issue has been present since the advent of surgery, there are a number of solutions in existence that address this problem. However, the existing systems have some significant drawbacks. Previous solutions to this problem include disposable towels, blankets, absorbent pads, and floor aspirators. Today, floor aspirators are the preferred tool for vacuuming fluids from the floor of an operating room, and the prior art teaches several different versions of these aspirators. However, even amongst these options that are in wide-spread use today, a number of problems still exist.

The first and foremost problem is the noise generated by current floor aspirators. While the suction source used by the floor aspirators is invariably loud, the actual attachment that makes contact with the floor acts as a secondary source of noise. In a situation where the instructions of a surgeon or a nurse should be heard, creating potential surgical error, additional noise generated is not beneficial and can be irritating to the operating staff. Further, the existing floor aspirators are almost uniformly circular, which leaves many areas of an operating room that cannot be directly aspirated.

Secondly, many of the floor aspirators don't properly collect fluid that gets spilled on top of the aspirator and as such, there is a need for a device that can quietly and effectively help aspirate fluids landing on top of the device as well as underneath of the device, while also being moved around the floor of the operating room safely.

Specific references to relevant prior art are herein described as follows:

U.S. Pat. No. 5,032,184 pertains to a method and apparatus for aspirating fluids from a surgical operating room utilizing a suction head that readily slides along the floor in response to translational forces applied by foot by operating room personnel. The suction head has a flat bottom surface with a plurality of narrow flow channels defined therein between a suction port mouth and the surface periphery. Support ribs, disposed on the top surface in juxtaposed alignment with respective flow channels, impart strength to the suction head and prevent sealing of the flow channels. The suction head is adapted to operate with suction sources commonly available in surgical operating rooms operating through a fluid waste collection chamber. The flow channels conduct fluid to be aspirated while preventing the bottom surface from becoming sealed to the floor.

U.S. Pat. No. 5,655,258 pertains to a suction device for removing liquids from a surface such as a floor. The device includes an air chamber formed from a top and a bottom plate, each of the plates having a respective top and bottom surface. The air chamber is in fluid communication with a fitting adjacent thereto. The bottom plate includes a plurality of holes therethrough. The bottom surface of the bottom plate additionally includes fabric adjacent thereto and feet to hold the bottom plate of the device up off the floor to enable fluid to be suctioned through the bottom plate holes and into the chamber via a conventional source of suction.

U.S. Pat. No. 5,741,237 pertains to a system for collecting and disposing of body fluids collected during surgery comprising a canister and a servicing unit for removing the body fluids from the canister and cleaning the canister for re-use. The canister is a vessel having sidewalls, a bottom and a lid. The lid has a first inlet port for the inflow of body fluids into the canister during surgery and a vacuum port for application of vacuum to the canister to induce the inflow of body fluids into the canister. The lid has a second inlet port for the inflow of cleaning fluid into the canister and a spray head in fluid communication with the second inlet port for spraying the cleaning fluid within the canister. The lid also has an outlet port with a suction tube extending into the canister for the outflow of body fluids and cleaning fluid from the canister. Caps are provided for closing those ports when the canister is being used to collect body fluids during surgery. The servicing unit has a first fluid conduit means to conduct fluid from the canister to a drain, and a second fluid conduit means to conduct cleaning fluid from a source of cleaning fluid to the second inlet port of the canister. There are connectors for connecting the first fluid conduit means to the outlet port of the canister and for connecting the second fluid conduit means to the second inlet port of the canister. Means are provided to control the flow of fluids through the fluid conduit means.

U.S. Pat. No. 5,720,078 pertains to a suction device for removing liquids from a surface such as a floor. The device includes an air chamber formed from a top and a bottom plate, each of the plates having a respective top and bottom surface. The air chamber is in fluid communication with a fitting adjacent thereto. The bottom plate includes a plurality of holes therethrough. The bottom surface of the bottom plate additionally includes fabric adjacent thereto and feet to hold the bottom plate of the device up off the floor to enable fluid to be suctioned through the bottom plate holes and into the chamber via a conventional source of suction. The device is also arranged to be located beneath an area where fluid is escaping for directly receiving and evacuating fluid that would otherwise fall on the floor.

U.S. Pat. No. 5,827,246 pertains to a system for collecting fluids from medical procedures, laboratory testing or industrial processes using a vacuum pad placed on the floor or an appropriate supporting structure adjacent to a potential source of hazardous fluids. The vacuum pad is formed from corrugated panels having a first sheet and a second sheet with a plurality of corrugated ribs to provide fluid flow channels between the first sheet and the second sheet. A manifold is provided as a part of the vacuum pad to supply a relatively uniform amount of vacuum to each fluid flow channel. The vacuum pad and a container for potentially hazardous fluids may be coupled in series by one or more conduits to a vacuum source such as commonly available in surgical operating rooms.

U.S. Pat. No. 6,136,098 pertains to a method for aspirating waste fluids from the floor of an operating room. A suction head may be placed on the floor and attached to an available negative pressure source. An elongated handle is selectively engageable with the suction head. The suction head can be selectively translated across the floor or lifted and moved to a pool of waste fluid with accuracy by using the handle. While this step is being done, the length of the elongated handle protects against contamination of the operator's limbs by the fluid falling from the surgical table. The handle is easily disengaged from the suction head when the suction head is positioned in a desirable location. The suction head suctions fluid under its bottom surface. Fluid falling on the top surface of the suction head is captured and directed through peripheral holes for aspiration beneath the suction head. Fluid suctioned through the suction head is then deposited safely in a waste collection chamber.

U.S. Pat. No. 7,901,389 pertains to an improved apparatus and method for aspirating liquids from surfaces particularly during medical procedures. Apparatus for removing liquid from a surface in the region of a medical procedure such as an operating room floor responsive to a drawn vacuum of preselected magnitude includes a plenum with an interior volume defined by an elongated box element with a plurality of supports member integral thereto or by an elongated tube, the plenum being perforated so as the exterior of the plenum is in direct liquid communication with the interior of the plenum, an absorptive wicking pad secured to the plenum so as to cover the perforations, an a vacuum conduit tube in direct vacuum communication with a vacuum collection system. A method of removal of liquids standing on surfaces such as operating room floors accomplished by positioning the disposable liquid removal apparatus with the exposed absorptive wicking pad down into the liquid, attaching the apparatus to a vacuum collection system, activating the system, and repositioning the apparatus as required.

United States Patent Publication No.: 2005/197639 pertains to an improved apparatus and method for aspirating liquids from surfaces particularly during medical procedures. Apparatus for removing liquid from a surface in the region of a medical procedure such as an operating room floor responsive to a drawn vacuum of preselected magnitude includes a plenum with an interior volume defined by an elongated box element with a plurality of supports member integral thereto or by an elongated tube, the plenum being perforated so as the exterior of the plenum is in direct liquid communication with the interior of the plenum, an absorptive wicking pad secured to the plenum so as to cover the perforations, an a vacuum conduit tube in direct vacuum communication with a vacuum collection system. A method of removal of liquids standing on surfaces such as operating room floors accomplished by positioning the disposable liquid removal apparatus with the exposed absorptive wicking pad down into the liquid, attaching the apparatus to a vacuum collection system, activating the system, and repositioning the apparatus as required.

United States Patent Publication No.: 2012/0210539 pertains to a repositionable fluid suction device. The device includes a central body and a suction channel located on an underside of the central body extending at least partially around a periphery of the central body. A rim extends downward from the central body, and may define a portion of the suction channel. A fluid collection trough extends at least partially around the periphery of the central body to collect fluids that fall on the upper surface of the central body. The outermost peripheral edge of the suction device may comprise at least one concave portion extending radially inward toward the central body.

Various devices are known in the art. However, their structure and means of operation are substantially different from the present disclosure. The other inventions fail to solve all the problems taught by the present disclosure. The present invention provides floor aspirators that are relatively quiet, safe to maneuver, inexpensive, and superior to the prior art. At least one embodiment of this invention is presented in the drawings below, and will be described in more detail herein.

SUMMARY OF THE EMBODIMENTS

The invention is a fluid aspirator, having a suction head having a perimeter, a top surface, a bottom surface, at least one drain between said top surface and said bottom surface, wherein said at least one drain spans between said top surface and said bottom surface, a suction port, comprising: a suction hole, and a fluid conduit; and a filter, disposed on said suction hole. In some embodiments, the invention further comprises a plurality of feet disposed on said bottom surface, and in others it further comprises at least one reinforcement rib, disposed on said top surface. Preferably, the at least one reinforcement rib is bisected by said suction port. In many embodiments said filter is constructed out of a reticulated foam mesh, and in others said suction port is located in the center of said suction head.

The present invention also provides for a fluid aspirator, comprising a quadrilateral component, having a perimeter, a top surface, a bottom surface, at least one drain between said top surface and said bottom surface, further having at least one chamfer between said top surface and said bottom surface, wherein said top surface is graded towards said at least one chamfer; at least one suction port, having a suction hole, and a fluid conduit and a filter, each filter being disposed on the suction hole. In other embodiments, the present invention contains a plurality of suction ports, each equipped with its own respective filter.

The present invention meets and exceeds the following objectives:

It is an object of the present invention to provide an improved apparatus for collecting fluids off of an operating room floor.

It is an object of the present invention to collect fluids dripping from and operating table.

It is an object of the present invention to provide an improved floor aspirator.

It is an object of the present invention to provide an inexpensive, disposable floor aspirator.

It is an object of the present invention to provide a floor aspirator that is quiet.

It is an object of the present invention to provide a floor aspirator that is safe.

DESCRIPTION OF THE PREFERRED EMBODIMENTS

The preferred embodiments of the present invention will now be described with reference to the drawings. Identical elements in the various figures are identified with the same reference numerals.

Reference will now be made in detail to each embodiment of the present invention. Such embodiments are provided by way of explanation of the present invention, which is not intended to be limited thereto. In fact, those of ordinary skill in the art may appreciate upon reading the present specification and viewing the present drawings that various modifications and variations can be made thereto.

While this disclosure refers to exemplary embodiments, it will be understood by those skilled in the art that various changes may be made and equivalents may be substituted for elements thereof without departing from the scope of the disclosure. In addition, many modifications will be appreciated by those skilled in the art to adapt a particular instrument, situation or material to the teachings of the disclosure without departing from the spirit thereof.

Therefore, it is intended that the disclosure not be limited to the particular embodiments disclosed.

Figure 1:
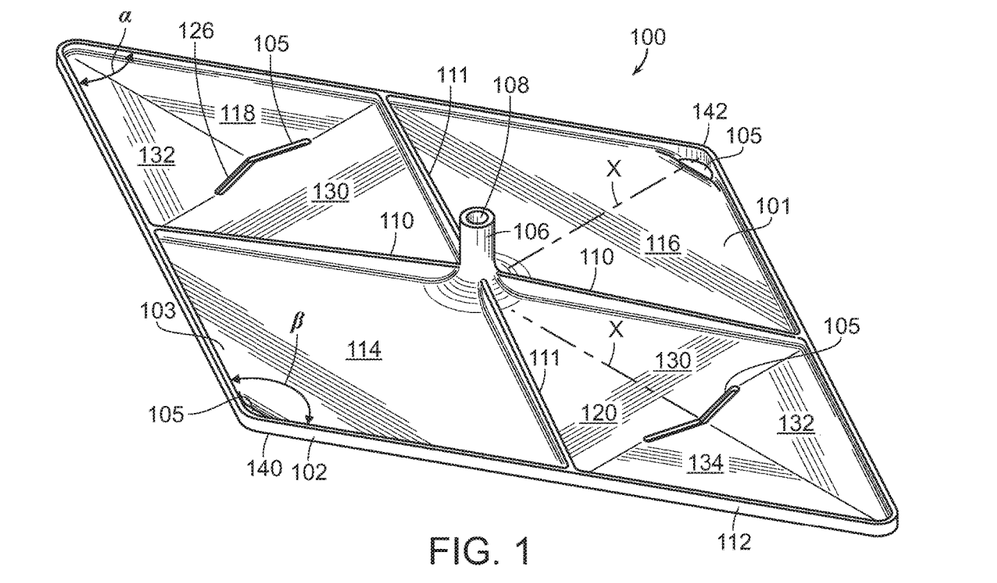
FIG. 1 shows a perspective view of an embodiment of the present invention.
Figure 2:
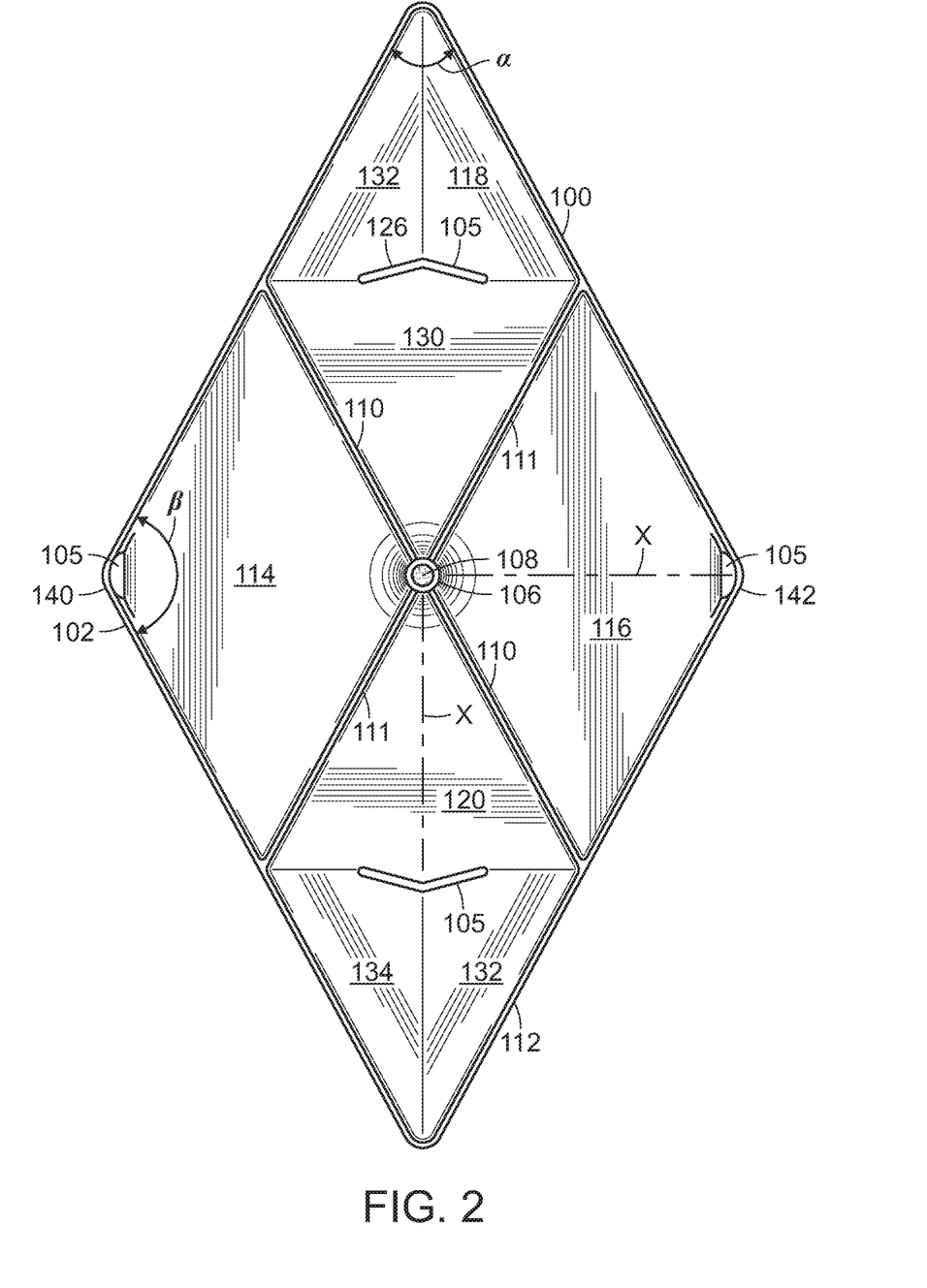
FIG. 2 shows a top view of an embodiment of the invention.

Referring to FIGS. 1 and 2, perspective and top views of an embodiment of the present invention are shown. Here, fluid aspirator 100 features suction head 101, perimeter 102, top surface 103, at least one drain 105, suction port 106, fluid conduit 108, reinforcement rib 111, and lip 112. Of note here is the inclusion of two reinforcement ribs 110, and 111 and lip 112. Suction head 101 is a generally planar shape. When the present invention is equipped with both of these features, the top surface of the suction head 101 is partitioned into four sections, 114, 116, 118 and 120. Preferably, there is one drain 105 in each of these partitions. In these embodiments, as well as other embodiments, the top surface of suction head is graded such that any fluids that fall onto this top surface will naturally flow to, and through, at least one drain 105. Further, reinforcement rib 111 and lip 112 both provide added structural integrity to fluid aspirator 100. In this configuration, fluid aspirator 100 is ideally operated by sliding or otherwise pushing fluid aspirator 100 around, this added structural integrity serves a beneficial purpose. Further, suction head 101 allows fluid aspirator 100 to vacuum fluids away from areas that the circular aspirators known in the part are incapable of reaching. Moreover, while a handle may be affixed to the present invention, no handle is need to move the fluid aspirator on the floor. The suction head 101 may have a thickness up to 1", but is preferably between 0.01" and 1" thick, more preferably between 0.05" and 0.5" thick. Here, suction head 101 has four corners, each having an edge and an angle. Preferably, the edge is rounded, but it can also be straight or edged. As seen in FIG. 1, corners have angles Alpha and Beta. The angles of Alpha can range from 10-90°, preferable 50-60°, most preferably 55°. Beta can range from 90-170°, 120-130°, preferably 125°. In addition suction head 101 can be a square, rectangle, parallelogram, kite shaped, trapezoid, rhombus, triangle or any other quadrilateral or triangle, hexagon, polygon, circle, oval or star shape Combinations of these shapes are also possible. In a preferred embodiment, the suction head 101 is diamond shaped.

Sections 118 and 120 each have drains 105. In a preferred embodiment, sections 118 and 120 have three graded surfaces, 130, 132, and 134. Graded surfaces 130, 132, and 134 drain toward drain 105. The graded surfaces can be separated by reinforcement ribs 110 and 111. Opposing sections 114 and 116 preferably have drains 105. The drains may have a slope/angle from 0.5 to 3.5° and preferably have a 1° angle. In some embodiments, the fluid aspirator may have one graded surface or multiple graded surfaces. Preferably, each section has at least one graded surface. The graded surfaces are preferably flat surfaces, but could also be rounded or tapered. When fluid falls on the top surface it rolls down the graded surface to the drain, where it drains onto the floor and is suctioned up through the suction port into the vacuum system.

In an alternative embodiment, the present invention further comprises a lip disposed on said perimeter and in other alternative embodiments said four corners have rounded edges. In some embodiments said at least one drain is located within said lip. In various embodiments the lip has a height, and said height ranges from 0.5 centimeters to 2.5 centimeters. Preferably, said suction port is recessed from said bottom surface and is substantially perpendicular to said suction head but could also offset at different angles. In highly preferred embodiments, said top surface is graded towards said at least one drain, or at least one chamfer 136. This is an essential feature. In an alternative embodiment, said filter is glued to said suction hole. In many embodiments, an attachment mechanism configured to removably attach to said bottom surface such that said filter is secured to said suction hole recess is equipped.

The diamond shape is especially preferred as the longer ends defined by sections 118 and 120 provide enough surface area to be slid with a person's foot, and the opposite section is elongated and therefore able to access corners, and other hard to reach areas. The elongated shape of the support is a safety feature, because the elongated portion gives more surface area for a user's shoe to grip the floor aspirator and slide same to a new location. This is in contrast to circular versions which do not have as much surface area and are harder to grip with a user's shoe and have been known to cause slips and falls. The placement of the ribs and the rim also provide additional surfaces for a user's shoe to push or guide the fluid aspirator on the floor during use.

As shown in the attached drawings, the drains can be of different sizes and or shapes. For example drains 105 have a V shape and are located in the middle of sections 118 and 120, whereas the drains in section 116 and 114 are located in corners 140 and 142, respectively and have a triangular shape. In a preferred embodiment, the drains are located equidistantly from the suction port 106. Thus, the distance x between suction port 106 and each of the drains is the same. This distance x is calculated based on the vacuum strength of the operating vacuum. The drains should be located close enough to the suction port that fluid draining from the top of the suction head through the drains can be suctioned through the suction port 106. In most embodiments the drains are 2.5" to 5" inches from the suction port, most preferable about 3.5" from the suction port Referring to FIG. 2 a top view of fluid aspirator 100 is shown. Here, fluid aspirator 100 features suction port 106, and at least one drain 105. As can be seen, at least one drain 105 can be in the form of a chamfer, as a sloped hole, or any other form that will permit fluid draining from the top surface of fluid aspirator 100 through drain 105 to the bottom surface. Suction port 106 is what gets connected to a standard operating vacuum or any other type of suitable suction source. Preferably, suction port 106 will be sized to receive ¼" tubing, but the size may be altered to accommodate tubes of different diameters.

Figure 3:
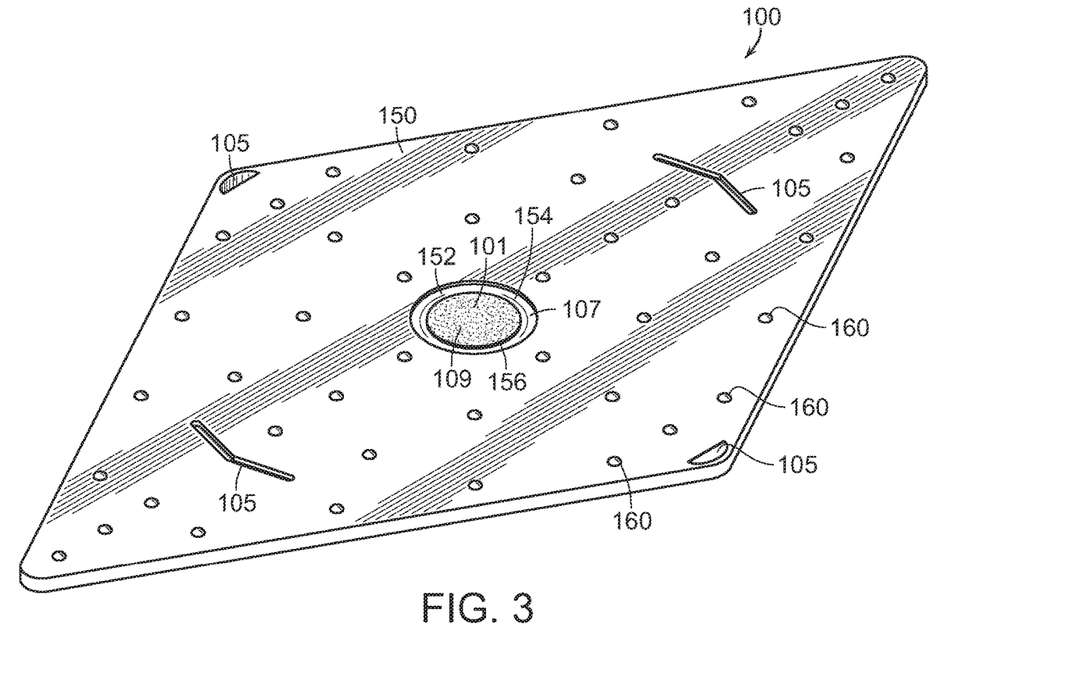
FIG. 3 shows a bottom perspective view of an embodiment of the present invention.
Figure 4:
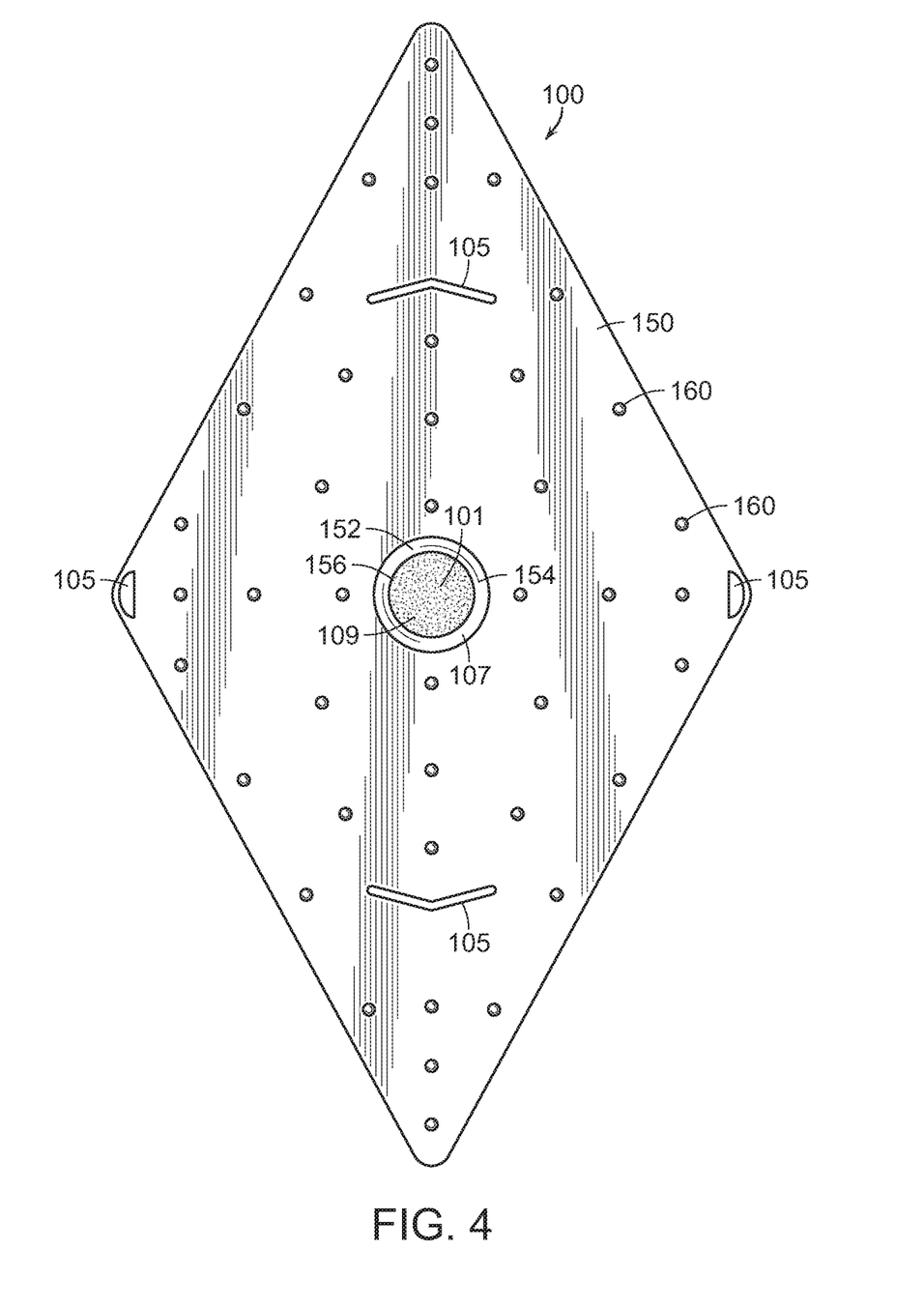
FIG. 4 shows a bottom view of an embodiment of the invention.

FIGS. 3 and 4 show a bottom perspective view and bottom view of an embodiment of the present invention. Here, fluid aspirator 100 features suction head 101, plurality of feet 160, filter 109, at least one drain 105, and suction port 106, and suction hole 107. This view shows how at least one drain 105 extends through the suction head 101. Also shown by this view is plurality of feet 110. While plurality of feet 160 are arranged in a particular way in this figure, many configurations are floor even while a vacuum is generated beneath fluid aspirator 100. The configuration of plurality of feet 100 also has an effect on the sound generated by operating fluid aspirator 100 with a vacuum attached to suction port 106. Also aiding in this noise reduction is the fact that in preferred embodiments suction hole 107 is recessed from the bottom surface of suction head 101. This recess allows for a wider volume of air to move through suction port 106 while generating reduced levels of noise. Shown in FIG. 3 is filter 109 disposed on suction hole 107. In preferred embodiments the bottom of the filter is flush to the bottom surface 150 of the suction head, or the filter extends slightly past the bottom surface but is shorter than plurality of feet 160 so the top of the filter does not scrape the floor. Also in preferred embodiments the diameter of the filter is slightly smaller than the diameter of the filter recess 152. There is a gap 154 between recess 152 and outer edge of filter 156. This allows fluid to enter the suction port through the side of the filter and also the bottom. Filter 109 prevents any solid matter from passing through suction port 106 and potentially damaging the vacuum source. While filter 109 may be constructed out of many materials, it is preferably constructed out of reticulated polyurethane foam. Preferably, fluid conduit 108 is sloped at the junction of fluid conduit 108 and suction hole 107. This provides improved fluid dynamics and allows for greater effective suction. Preferably, suction hole 107 is recessed from the bottom surface of suction head 101.

Figure 5:
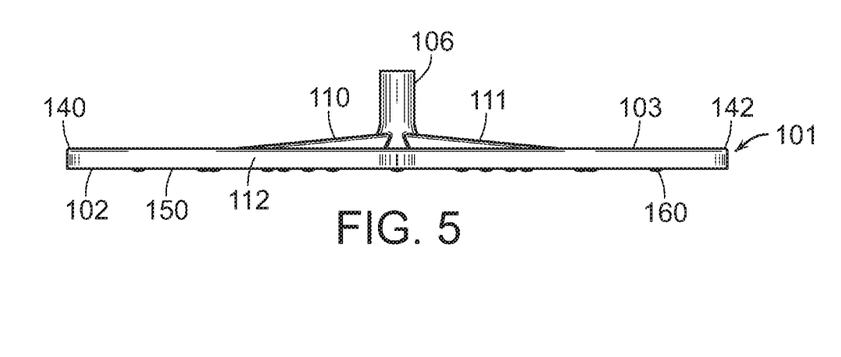
FIG. 5 shows a side view of an embodiment of the invention.
Figure 6:
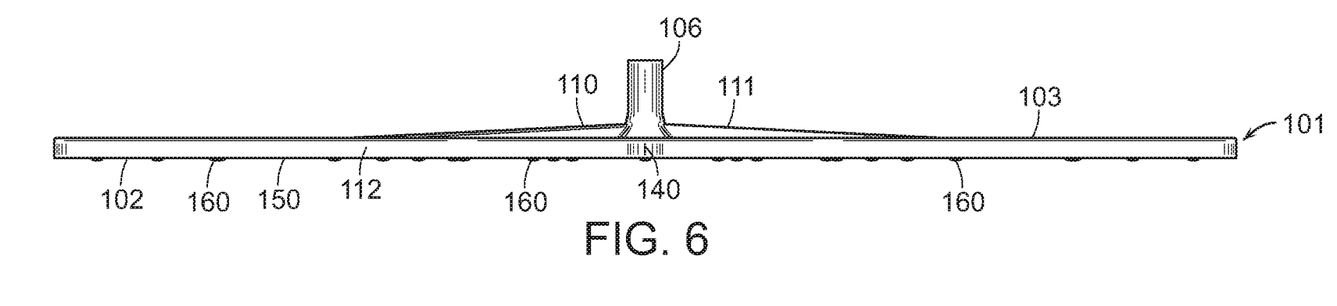
FIG. 6 shows a side view of an embodiment of the invention.

FIGS. 5 and 6 show side views of the invention, including substantially planer suction head 101, suction port 106, reinforcement ribs 110 and 111, perimeter 102, corners 140 and 142, top surface 103, bottom surface 150 and plurality of feet 160.

Many materials are suitable for use in the present invention, but preferably said fluid aspirator is constructed out of a material selected from the group consisting essentially of: PET, HDPE, PVC, LDPE, PP, HIPS, PS, PC, PA, PCDC, ABS, PU, PC/ABS. In various embodiments, the present invention in constructed out of polyester (PES), polyethylene terephthalate (PET), polyethylene (PE), high-density polyethylene (HDPE), polyvinylchloride (PVC), polyvinylidene chloride (PVDC), low-density polyethylene (LDPE), polypropylene (PP), polystyrene (PS), high-impact polystyrene (HIPS), polyamides (PA), acrylonitrile butadiene styrene (ABS), polyethylene/acrylonitrile butadiene styrene (PE/ABS), polycarbonate (PC), polyurethanes (PU), or some combination thereof.

In an alternative embodiment, the present invention has multiple suction ports. In another embodiment, the present invention is equipped with an absorbent material covering the entire bottom or top surface of the fluid aspirator. The absorbent material can be any absorbent material or moisture wicking material but could be polypropylene, polyethylene, cotton, nylon or blends thereof. This provides greater aspiration of fluids from a floor. The fluid aspirator can come in multiple colors.

When introducing elements of the present disclosure or the embodiment(s) thereof, the articles "a," "an," and "the" are intended to mean that there are one or more of the elements. Similarly, the adjective "another," when used to introduce an element, is intended to mean one or more elements. The terms "including" and "having" are intended to be inclusive such that there may be additional elements other than the listed elements.

Therefore, it is intended that the disclosure not be limited to the particular embodiments disclosed.

What is claimed is:

1. A fluid aspirator, comprising:
 a substantially planar suction head having:
  four corners, each corner having an edge and an angle,
  a perimeter,
  a top surface,
  a bottom surface,
  at least one drain between said top surface and said bottom surface,
   wherein said at least one drain spans between said top surface and said bottom surface,
  a suction port being recessed from said bottom surface, said suction port having:
   a suction hole being recessed from said bottom surface,
   a fluid conduit; and
  a filter, disposed on said suction hole.

2. The fluid aspirator of claim 1, further comprising a plurality of feet disposed on said bottom surface.

3. The fluid aspirator of claim 1, further comprising at least one reinforcement rib, disposed on said top surface.

4. The fluid aspirator of claim 3, wherein said at least one reinforcement rib is bisected by said suction port.

5. The fluid aspirator of claim 1, wherein said filter is constructed out of a reticulated foam mesh.

6. The fluid aspirator of claim 1, wherein said suction port is located in the center of said suction head.

7. The fluid aspirator of claim 1, wherein said fluid aspirator is constructed out of a material selected from the group consisting essentially of: PET, HDPE, PVC, LDPE, PP, HIPS, PC, PA, PCDC, ABS, PU, PC/ABS, and PS.

8. The fluid aspirator of claim 1, further comprising a lip disposed on said perimeter.

9. The fluid aspirator of claim 8, wherein said at least one drain is located proximate to said lip.

10. The fluid aspirator of claim 8, wherein said lip has a height, and said height ranges from 0.5 centimeters to 2.5 centimeters.

11. The fluid aspirator of claim 1, wherein said suction port is substantially perpendicular to said suction head.

12. The fluid aspirator of claim 1, wherein said top surface is graded towards said at least one drain.

13. The fluid aspirator of claim 1, wherein said filter is glued or adhered to said suction hole.

14. The fluid aspirator of claim 1, further comprising an attachment mechanism configured to removably attach to said bottom surface such that said filter is secured to said suction hole.

15. The fluid aspirator of claim 1, wherein two of the four corners have an angle of 55° and two of the four corners have an angle of 125°.

16. The fluid aspirator of claim 1, further comprising an absorbent material disposed on said top surface or said bottom surface.

17. A fluid aspirator, comprising:
a quadrilateral component, comprising:
  a perimeter,
  a top surface having ribbing, with the ribbing dividing the top surface into sections,
  a bottom surface,
  at least one drain disposed in each of the sections, the at least one drain being between said top surface and said bottom surface,
  wherein said at least one drain between said top surface and said bottom surface,
  wherein said top surface is graded towards said at least one drain;
at least one suction port, having:
  a suction hole, and
  a fluid conduit; and
a filter, each filter being disposed on the suction hole.

18. The fluid aspirator of claim 17 wherein the ribbing divides the top surface into four sections.

19. The fluid aspirator of claim 18 wherein the at least one drain is disposed along a periphery of the aspirator in two of the four sections and wherein the at least one drain is disposed in a central portion in two of the four sections.

20. The fluid aspirator of claim 19 wherein each of the drains are located equidistant from the suction port.

21. The fluid aspirator of claim 19 wherein the top surface of each section is graded towards the at least one drain disposed in that section.

\* \* \* \* \*